United States Patent
Qiang et al.

(10) Patent No.: US 11,835,668 B2
(45) Date of Patent: Dec. 5, 2023

(54) SUMMING CIRCUIT FOR POSITRON EMISSION TOMOGRAPHY DIAGNOSTIC APPARATUS

(71) Applicant: CANON MEDICAL SYSTEMS CORPORATION, Otawara (JP)

(72) Inventors: Yi Qiang, Vernon Hills, IL (US); Kent C. Burr, Vernon Hills, IL (US); Peng Peng, Vernon Hills, IL (US); Xiaoli Li, Vernon Hills, IL (US)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 0 days.

(21) Appl. No.: 17/345,823

(22) Filed: Jun. 11, 2021

(65) Prior Publication Data

US 2022/0397688 A1 Dec. 15, 2022

(51) Int. Cl.
*A61B 6/03* (2006.01)
*G01T 1/29* (2006.01)
*A61B 6/00* (2006.01)

(52) U.S. Cl.
CPC ............ *G01T 1/2985* (2013.01); *A61B 6/037* (2013.01); *A61B 6/5258* (2013.01)

(58) Field of Classification Search
CPC ............................. A61B 6/037; A61B 6/5258
See application file for complete search history.

(56) References Cited

U.S. PATENT DOCUMENTS

| | | | |
|---|---|---|---|
| 6,263,095 B1 * | 7/2001 | Rushbrooke | G01N 21/6456 382/172 |
| 6,333,503 B1 * | 12/2001 | Chapuis | G01T 1/1642 250/369 |
| 9,513,378 B2 | 12/2016 | Roknsharifi | |
| 9,903,961 B1 | 2/2018 | Ng et al. | |
| 9,945,965 B2 | 4/2018 | Fu et al. | |
| 10,310,098 B1 * | 6/2019 | Qiang | G01T 1/202 |
| 2006/0192128 A1 * | 8/2006 | Benlloch Bavciera | G01T 1/1642 250/369 |
| 2012/0307025 A1 * | 12/2012 | Werner Lerche | G01T 1/1647 348/61 |

(Continued)

FOREIGN PATENT DOCUMENTS

EP 3591440 A1 1/2020

OTHER PUBLICATIONS

Krishnakumar Scintillation screen materials for beam profile measurements of high energy ion beams, Technische Universitat Daemstadt Dissertation, 140 pages (Year: 2016).*

(Continued)

*Primary Examiner* — David P Porta
*Assistant Examiner* — Mamadou Faye
(74) *Attorney, Agent, or Firm* — Oblon, McClelland, Maier & Neustadt, L.L.P.

(57) ABSTRACT

A circuit for receiving signals from a photodetector array arranged to detect signals generated by a crystal includes a plurality of summing circuits having weighting circuits, the summing circuits being configured to produce outputs corresponding to a total energy of the signals, a position of the signals in a first dimension of the photodetector array, a position of the signals in a second dimension of the photodetector array, and a radius of a charge distribution of the signals.

16 Claims, 12 Drawing Sheets

(56) References Cited

U.S. PATENT DOCUMENTS

| 2013/0214168 | A1* | 8/2013 | McDaniel | G01T 1/2985 |
| | | | | 250/362 |
| 2014/0224963 | A1* | 8/2014 | Guo | G01T 1/2985 |
| | | | | 250/208.1 |
| 2017/0329021 | A1* | 11/2017 | Bircher | G01T 1/208 |
| 2020/0233101 | A1* | 7/2020 | Nakazawa | A61B 6/485 |
| 2021/0141102 | A1* | 5/2021 | Dissertori | H01L 27/14609 |

OTHER PUBLICATIONS

Y. C. Shih, F. W. Sun, L. R. MacDonald, B. P. Otis, R. S. Miyaoka, W. McDougald, T. K. Lewellen. "An 8x8 row-column summing readout electronics for preclinical positron emission tomography scanners." https://www.ncbi.nlm.nih.gov/pmc/articles/PMC2923847/. Oct. 24, 2009.

* cited by examiner

| SiPM Location | | Weights | | | |
|---|---|---|---|---|---|
| x | y | W_X | W_Y | W_E | W_R |
| 1 | 1 | 1 | 1 | 1 | 2 |
| 2 | 1 | 2 | 1 | 1 | 5 |
| 3 | 1 | 3 | 1 | 1 | 10 |
| 4 | 1 | 4 | 1 | 1 | 17 |
| 1 | 2 | 1 | 2 | 2 | 5 |
| 2 | 2 | 2 | 2 | 2 | 8 |
| 3 | 2 | 3 | 2 | 2 | 13 |
| 4 | 2 | 4 | 2 | 2 | 20 |
| 1 | 3 | 1 | 3 | 3 | 10 |
| 2 | 3 | 2 | 3 | 3 | 13 |
| 3 | 3 | 3 | 3 | 3 | 18 |
| 4 | 3 | 4 | 3 | 3 | 25 |
| 1 | 4 | 1 | 4 | 4 | 17 |
| 2 | 4 | 2 | 4 | 4 | 20 |
| 3 | 4 | 3 | 4 | 4 | 25 |
| 4 | 4 | 4 | 4 | 4 | 32 |

FIG. 9

| 1 | 2 | 3 | 4 |
|---|---|---|---|
| 1 | 2 | 3 | 4 |
| 1 | 2 | 3 | 4 |
| 1 | 2 | 3 | 4 |

| 1 | 1 | 1 | 1 |
|---|---|---|---|
| 2 | 2 | 2 | 2 |
| 3 | 3 | 3 | 3 |
| 4 | 4 | 4 | 4 |

| 1 | 1 | 1 | 1 |
|---|---|---|---|
| 1 | 1 | 1 | 1 |
| 1 | 1 | 1 | 1 |
| 1 | 1 | 1 | 1 |

| 2 | 5 | 10 | 17 |
|---|---|---|---|
| 5 | 8 | 13 | 20 |
| 10 | 13 | 18 | 25 |
| 17 | 20 | 25 | 32 |

| | X | | Hit 1 | Hit 2 | Summed Output | | Decoded Position | |
|---|---|---|---|---|---|---|---|---|
| Case 1 | | x | 1 | n/a | $X_{sum}$ | 1 | X | 1 |
| | | y | 1 | n/a | $Y_{sum}$ | 1 | Y | 1 |
| | | $E_i$ | 1 | 0 | $E_{sum}$ | 1 | E | 1 |
| | | | | | $R_{sum}$ | 2 | R | 0 |
| Case 2 | | x | 2 | n/a | $X_{sum}$ | 2 | X | 2 |
| | | y | 2 | n/a | $Y_{sum}$ | 2 | Y | 2 |
| | | $E_i$ | 1 | 0 | $E_{sum}$ | 1 | E | 1 |
| | | | | | $R_{sum}$ | 8 | R | 0 |
| Case 3 | | x | 2 | 3 | $X_{sum}$ | 2.5 | X | 2.5 |
| | | y | 2 | 2 | $Y_{sum}$ | 2 | Y | 2 |
| | | $E_i$ | 0.5 | 0.5 | $E_{sum}$ | 1 | E | 1 |
| | | | | | $R_{sum}$ | 10.5 | R | 0.25 |
| Case 4 | | x | 1 | 4 | $X_{sum}$ | 2.5 | X | 2.5 |
| | | y | 1 | 1 | $Y_{sum}$ | 1 | Y | 1 |
| | | $E_i$ | 0.5 | 0.5 | $E_{sum}$ | 1 | E | 1 |
| | | | | | $R_{sum}$ | 9.5 | R | 2.25 |
| Case 5 | | x | 1 | 4 | $X_{sum}$ | 2.5 | X | 2.5 |
| | | y | 1 | 3 | $Y_{sum}$ | 2 | Y | 2 |
| | | $E_i$ | 0.5 | 0.5 | $E_{sum}$ | 1 | E | 1 |
| | | | | | $R_{sum}$ | 13.5 | R | 3.25 |
| Case 6 | | x | 4 | 1 | $X_{sum}$ | 2.5 | X | 2.5 |
| | | y | 2 | 4 | $Y_{sum}$ | 3 | Y | 3 |
| | | $E_i$ | 0.5 | 0.5 | $E_{sum}$ | 1 | E | 1 |
| | | | | | $R_{sum}$ | 18.5 | R | 3.25 |

FIG. 12

SUMMING CIRCUIT FOR POSITRON EMISSION TOMOGRAPHY DIAGNOSTIC APPARATUS

BACKGROUND OF THE INVENTION

Field of the Invention

The present disclosure relates to a summing circuit and method for Positron Emission Tomography (PET) diagnostic apparatus.

Description of the Related Art

A conventional PET detector uses a crystal array to determine the position of incident gamma rays. Silicon photomultipliers (SiPMs) are used with the crystal array, allowing the crystal array to be fully coupled with the detector array formed with pixelated photodetectors. Signals from the SiPMs of an array are either digitized individually or summed with weights so that the resulting signals correspond to the total energy of the signal and the two-dimensional (2D) coordinates of the detected gamma ray.

Due to scatter and light sharing between crystals and SiPMs, an incident gamma ray may sometimes be detected by multiple SiPMs, causing charge distribution across an array. This charge distribution can provide useful information to improve timing resolution and spatial resolution. A schematic diagram of scattering is shown in FIG. 1. A 511 keV photon is received at one crystal 10a and scattered indicated by arrow 20 to another crystal 10b. The charge from the crystal 10 received by SiPM 30 is shown schematically by curves 40 and 41.

It is also possible to use a monolithic crystal. The charge distribution can be used to derive the depth of interaction (DOI). FIG. 2 illustrates the monolithic crystal scattering and charge sharing information. 511 keV photons at different depths are adsorbed by the monolithic crystal 50 and detected by SiPM 70. The charge distributions for the two photons are shown as 80 and 81. The DOI is indicated as 60.

In order to obtain higher spatial resolution, smaller crystals are needed resulting in a higher number of SiPMs. With significantly more SiPMs to read out, Anger logic may be used to reduce the total number of outputs. However, the use of Anger logic results in loss of the charge distribution.

A conventional weighted summing circuit is found in U.S. Pat. No. 9,945,965. The readout circuit is illustrated in FIG. 2 of the patent. In this system there are only two sum channels for position information which limits the information available from the crystal array.

SUMMARY OF THE INVENTION

An embodiment of the present invention is directed to a circuit for receiving signals from a photodetector array arranged to detect signals generated by a crystal includes a plurality of summing circuits having weighting circuits, the summing circuits configured to produce outputs corresponding to a total energy of the signals, a position of the signals in a first dimension of the photodetector array, a position of the signals in a second dimension of the photodetector array, and a radius of a charge distribution of the signals.

Another embodiment of present invention is directed to a positron emission apparatus having a crystal configured to receive gamma rays and a photodetector array arranged to detect signals generated by the crystal. A circuit is connected to the photodetector array and includes a plurality of summing circuits having weighting circuits, the summing circuits configured to produce outputs corresponding to a total energy of the signals, a position of the signals in a first dimension of the photodetector array, a position of the signals in a second dimension of the photodetector array, and a radius of a charge distribution of the signals.

A further embodiment of present invention is directed to a method of extracting information from gamma interactions within a crystal including producing output signals from the interactions and producing a first signal corresponding to a total energy of the output signals, a second signal corresponding to the energy of the output signals weighted according to a position of the output signals in a first dimension of the crystal, a third signal corresponding to the energy of the output signals weighted according to a position of the output signals in a second dimension of the crystal, and a fourth signal corresponding to the energy of the output signals weighted according to a variance of the positions of the output signals in the first and second directions.

A still another embodiment of present invention is directed to a method of determining positions of gamma ray interactions in a crystal. The method includes producing output signals from the interactions and producing a first signal corresponding to a total energy of the output signals, a second signal corresponding to the energy of the output signals weighted according to a position of the output signals in a first dimension of the crystal, a third signal corresponding to the energy of the output signals weighted according to a position of the output signals in a second dimension of the crystal, and a fourth signal corresponding to the energy of the output signals weighted according to a variance of the positions of the output signal in the first and second directions. A position of an interaction is determined using at least one of a ratio of the second signal to the first signal, a ratio of the third signal to the first signal, and a ratio of a sum of the square of the first signal and the square of the second signal to a square of the first signal subtracted from a ratio of the fourth signal to the first signal.

BRIEF DESCRIPTION OF THE DRAWINGS

The application will be better understood in light of the description which is given in a non-limiting manner, accompanied by the attached drawings in which:

FIG. 9 is a chart illustrating weights used in an example photodetector array;

FIGS. 10A-10D show the weights by readout channels in the photodetector array;

FIG. 12 is a chart illustrating position decoding using the summing circuit according to the invention;

DETAILED DESCRIPTION OF THE PREFERRED EMBODIMENTS

Figure 3:
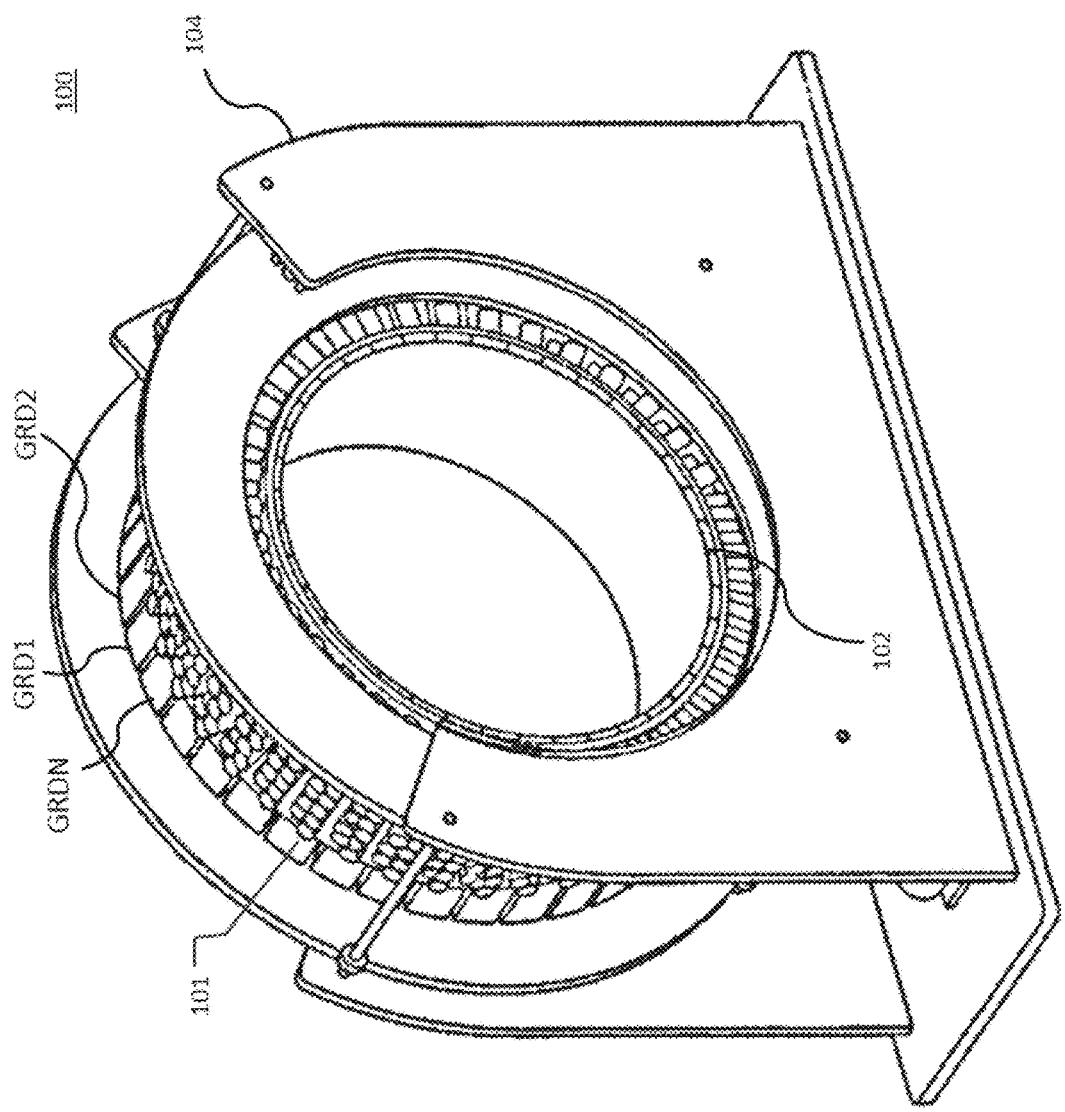
FIG. 3 is an illustration of a perspective view of a positron emission tomography (PET) scanner according to the invention.
Figure 4:
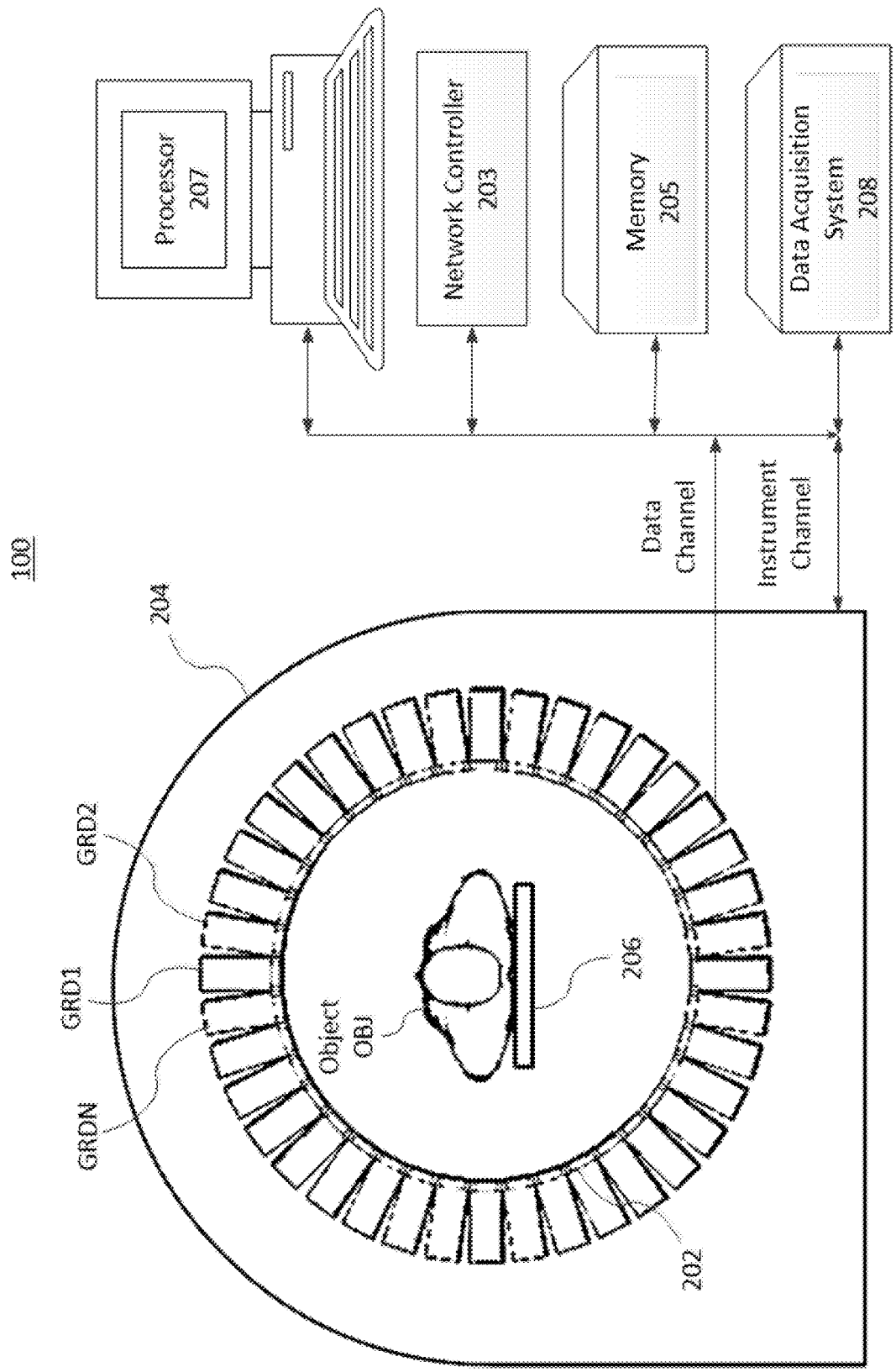
FIG. 4 is a schematic of a PET scanner apparatus and associated hardware, according to an exemplary embodiment of the present disclosure.

A PET scanner according to the invention is shown in FIGS. 3-4. PET scanner 100 includes a plurality of gamma-ray detectors (GRDs) 101 (e.g., GRD1, GRD2, through GRDN) that are each configured as rectangular detector modules. According to one implementation, the detectors are arranged in a ring, which forms a circular bore 102 about a gantry 104. In this example, the ring includes 40 GRDs 101. A ring may have a different number of GRDs 101 depending on factors such as the desired size of bore 102. The GRDs 101 include scintillator crystal arrays for converting the gamma rays into scintillation photons (e.g., at optical, infrared, and ultraviolet wavelengths), which are detected by photodetectors. Each GRD 101 can include a two-dimensional array of individual detector crystals, which absorb gamma radiation and emit scintillation photons, or can include a monolithic array or a slatted array. The scintillation photons can be detected by a two-dimensional array of devices such as SiPMs (not shown) that are also arranged in the GRD 101. A light guide can be disposed between the array of detector crystals and the SiPMs. The crystal and SiPM arrangements according to the invention are discussed in more detail below.

FIG. 3 shows a schematic view of a PET scanner system having GRDs arranged to detect gamma-rays emitted from an object OBJ. The GRDs can measure the timing, position, and energy corresponding to each detected gamma-ray. It can be appreciated that the single PET detector ring of FIG. 3 can be extrapolated to include any number of PET detector rings along an axial length of the PET scanner.

FIG. 4 shows an example of the arrangement of a PET scanner 100, in which the object OBJ to be imaged rests on a table 206 and the GRD modules GRD1 through GRDN are arranged circumferentially around the object OBJ and the table 206. The GRDs may comprise a PET detector ring and may be fixedly-connected to a cylindrical bore 202 that is fixedly-connected to a gantry 204. The gantry 204 houses many parts of the PET scanner. The gantry 204 of the PET scanner also includes an open aperture, defined by the cylindrical bore 202, through which the object OBJ and the table 206 can pass, and gamma-rays emitted in opposite directions from the object OBJ due to an annihilation event can be detected by the GRDs and timing and energy information can be used to determine coincidences for gamma-ray pairs.

In FIG. 4, circuitry and hardware are also shown for acquiring, storing, processing, and distributing gamma-ray detection data. The circuitry and hardware include a processor 207, a network controller 203, a memory 205, and a data acquisition system (DAS) 208. The PET imager also includes a data channel that routes detection measurement results from the GRDs to the DAS 208, the processor 207, the memory 205, and the network controller 203. The DAS 208 can control the acquisition, digitization, and routing of the detection data from the detectors. In one implementation, the DAS 208 controls the movement of the table 206. The processor 207 performs functions including identifying arrangement errors, pre-reconstruction processing of the detection data, image reconstruction, and post-reconstruction processing of the image data.

According to an embodiment, the processor 207 of the PET scanner 100 of FIGS. 3 and FIG. 4 can be configured to perform the methods as described herein. The processor 207 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory 305 can be a hard disk drive, CD-ROM drive, DVD drive, FLASH drive, RAM, ROM or any other electronic storage known in the art. The memory 205 may be non-volatile, such as ROM, EPROM, EEPROM or FLASH memory. The memory 205 can also be volatile, such as static or dynamic RAM, and a processor, such as a microcontroller or microprocessor, may be provided to manage the electronic memory as well as the interaction between the FPGA or CPLD and the memory.

Alternatively, the CPU in the processor 207 can execute a computer program including a set of computer-readable instructions that perform methods described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel or an Opteron processor from AMD and an operating system, such as Microsoft VISTA, UNIX, Solaris, LINUX, Apple, MAC-OS and other operating systems known to those skilled in the art. Further, the CPU can be implemented as multiple processors cooperatively working in parallel to perform the instructions. The instructions may be stored in memory 205 or within a memory located in network controller 203 (not shown).

In one implementation, the PET scanner may include a display for displaying a reconstructed image and the like. The display can be an LCD display, CRT display, plasma display, OLED, LED or any other display known in the art.

The network controller 203, such as an Intel Ethernet PRO network interface card from Intel, can interface between the various parts of the PET imager. Additionally, the network controller 203 can also interface with an external network. As can be appreciated, the external network can be a public network, such as the Internet, or a private network such as an LAN or WAN network, or any combination thereof and can also include PSTN or ISDN sub-networks. The external network can also be wired, such as an Ethernet network, or can be wireless such as a cellular network including EDGE, 3G and 4G wireless cellular systems. The wireless network can also be WiFi, Bluetooth, or any other wireless form of communication that is known.

Figure 5A:
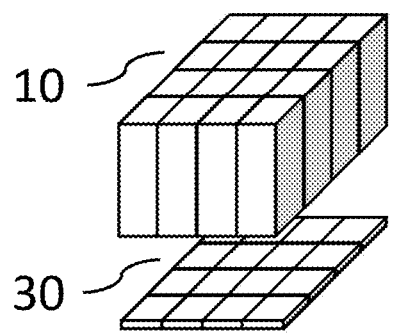
FIGS. 5A-5D are diagrams illustrating arrangements of the crystal detector and the photodetector array.
Figure 5B:
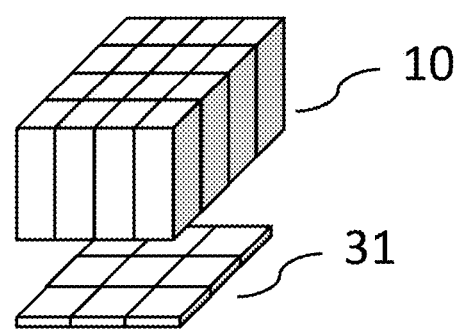
Figure 5C:
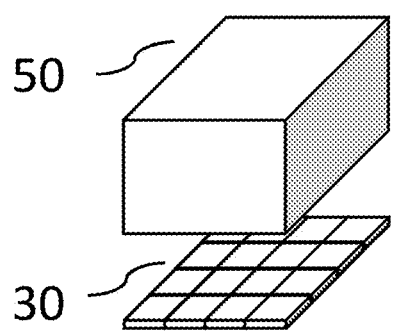
Figure 5D:
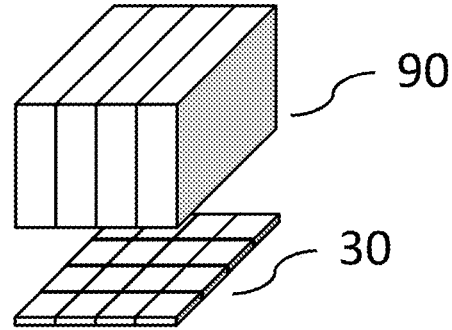

In the GRD detector 101 according to the invention, a photodetector such as an SiPM array is coupled to a crystal array, a stack of crystal slats or a monolithic crystal. These structures are shown in FIGS. 5A-5D. The figures are examples and show a representative number of crystals and SiPM elements. The number of crystals and SiPM elements can vary according to the needs and requirements of the PET apparatus. FIGS. 5A and 5B show the crystal array 10 coupled to SiPM arrays 30 and 31 with 1-1 coupling and mismatched coupling, where the number of crystals and the number of SiPMs differ, respectively. In the example of FIG. 3B, the SiPM array 30 has a greater pitch (or fewer elements) than the number of crystals in the array. The SiPM array 30 is made up of detector elements while the crystal array 10 is made up of a number of crystals. The embodiment using a monolithic crystal is illustrated in FIG. 5C and the embodiment with array 90 using slat crystals is illustrated in FIG. 5D.

In the crystal arrays the crystals may be isolated from each other by an air gap, reflector or opaque materials. The separation between the crystals does not have to completely segregate the light transmitting through the crystal. Some light sharing between crystals may be allowed, for example when there is a shorter reflector arranged in the gaps than the length of the crystal.

The signals from the individual channels of the photodetector array are summed to derive information about the received signals. In the present invention, the signals from the photodetector array are advantageously fed into a plurality of summing groups with specially designed weights. The summing circuits are part of the DAS 208 or, alternatively, may be located in the GRDs. For example, four or more summing groups may be arranged. In this example one group is designed to add equal weights to produce an energy signal. Two groups have channel dependent weights to produce a coordinate signal. A fourth group with channel dependent weights produces a radius signal for the charge distribution.

In principle, the distribution of charge can be expressed as the sum of all orders of moments. For a distribution of probability, charge distribution in this application, within a bounded interval, the collection of all the moments $(m_n = \int x^n f(x) dx$ of all the orders, n from 0 to $\infty$) uniquely determines the distribution (Hausdorff moment problem, Moment (mathematics)—Wikipedia; en.wikipedia.org/wiki/Moment_(mathematics)). Therefore more groups may be added if more characteristics of the charge distribution need to be extracted.

Figure 6A:
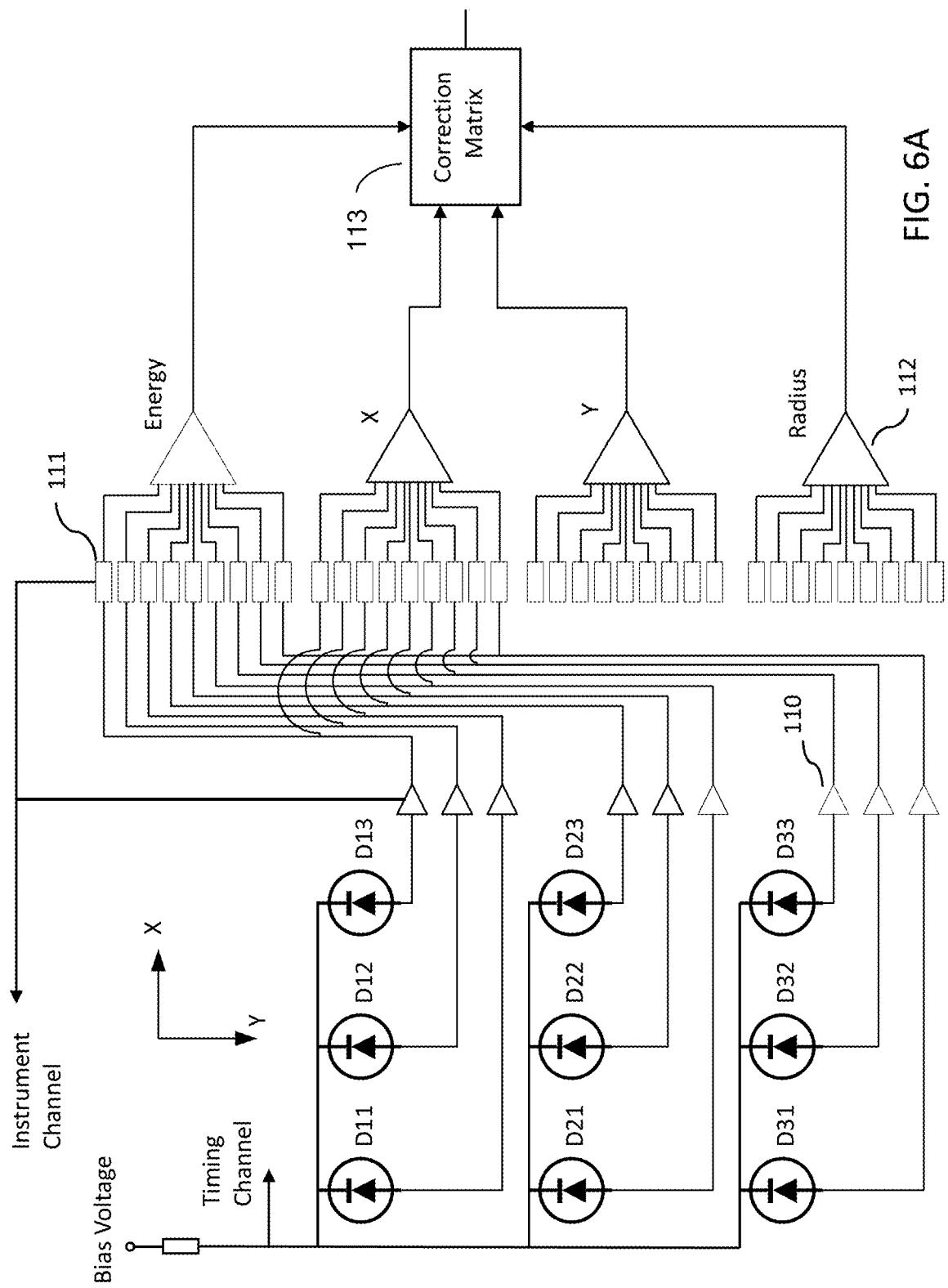
FIG. 6A is a diagram of a summing circuit according to a first embodiment of the invention.

A first example of the summing circuit according to the invention is illustrated in FIG. 6A. This arrangement is one-stage summing. SiPMs D11 through D33 arranged in a 3×3 matrix are shown as an example. Typically there are a much larger number of SiPMs to be summed Each of the outputs of the SiPMs is first buffered using buffers 110 and then forwarded to an array of weighting circuits 111. The buffers consist of amplifiers used to terminate the SiPM electrodes and drive the output for the weighting processing. A typical buffer used for the SiPM is a transimpedance input amplifier (TIA). It translates the current signal from the SiPM into a voltage signal having a desired amplitude. The weighting circuits 111 control the weights applied to the signals prior to being summed in a summing amplifier. The connections between the buffers 110 and the weighting circuits 111 are shown only for the Energy and X signals for ease of illustration. The outputs of the buffers connected to SiPMs D11-D33 are also fed to the weighting circuits 111 for the Y and Radius signals.

Figure 7:
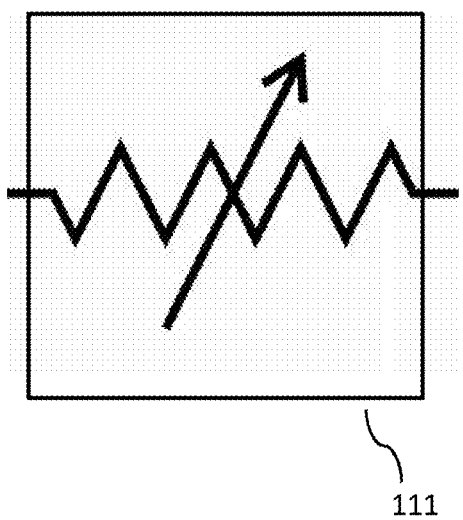
FIG. 7 is a diagram of a weighting circuit.

An example of the weighting circuit is shown in FIG. 7. The weights may be implemented as a variable resistor, or a variable impedance device, and are controllable by a processor. The weights are adjusted as desired to provide the appropriate input to the summing amplifier from the signal produced by the SiPMs. Control of the weighting circuits is described in more detail below.

Each of the weighting circuits 111 can be connected to the instrument channel and are controlled by processor 207 to set and adjust the appropriate weights. Also, the buffers 110 also can be connected to the instrument channel for control of the gain. The gain can be adjusted to compensate for variations in SiPM gain. It is also possible to adjust the weights to compensate for the variation in SiPM gain. In FIG. 6A only one buffer 110 and one weighting circuit 111 are shown as being connected to the instrument channel for ease of illustration.

The outputs of the weighting circuits are input to summing amplifiers 112 to provide the Energy signal. X and Y signals representing coordinate signals are produced with channel dependent weights, and the Radius signal is produced with channel dependent weights. The summing amplifiers aggregate the signals at the inputs and output a signal proportional to the sum of the input signals. For example, the voltage values of the signals output by the weighting circuits 111 are summed to produce a summed voltage value. The summed outputs are output to a correction matrix 113 which may consist of hardware, FPGA, a processor configured to execute programs either present in the processor or stored in memory 205, a translational table or neural network. The operation of the correction matrix is described in more detail below. Matrix 113 may be omitted and the summed outputs used without correction.

Figure 8:
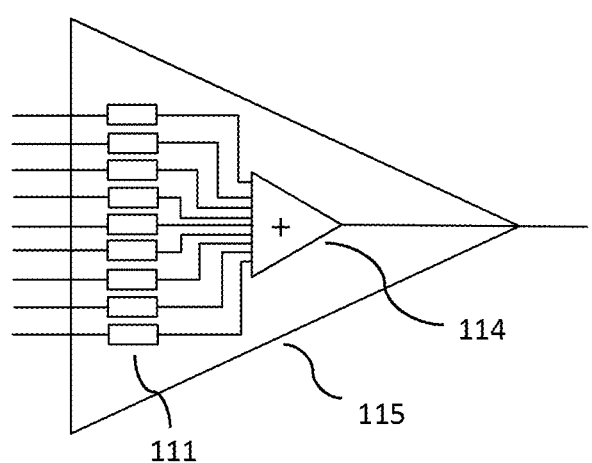
FIG. 8 is a diagram of a summing amplifier according to the invention.

In a modification of the first embodiment, the weighting circuits may be part of the summing amplifier. Summing amplifier 115 is shown in FIG. 8 having weighting circuits 111 and summer 114.

The weighting of the signals will now be described in more detail. For the energy channel an equal weight is used:

$E = \Sigma E_{xy}$

In this formula the indices x and y represents the 2 dimensional location of the SiPM in the SiPM array and $E_{xy}$ is the value of the signal from the buffer at position (x,y). For the x channel the weight is proportional to the horizontal position x and is given as:

$X = \Sigma x E_{xy}.$

Similarly, the Y channel the weight is proportional to the vertical position Y as given in the following formula:

$Y = \Sigma y E_{xy}$

Lastly, the radius channel the weight is proportional to $(x^2 + y^2)$ and is given by the following formula:

$R = \Sigma (x^2 + y^2) E_{xy}$

The summed variance of the charge distribution, which is an indicator of scatter or DOI(Z) can be derived by the processor 207 using the following formula:

$$\sigma^2 = \frac{R}{E} - \frac{X^2 + Y^2}{E^2}$$

In a modification, if variances of the charge distributions in both of the x and y directions need to be separated, two radius channels may be implemented as follows:

$R_x = \Sigma x^2 E_{xy}$ $R_y = \Sigma y^2 E_{xy}$

The summed variance in this modification is given as:

$$\sigma_x^2 = \frac{R_x}{E} - \frac{X^2}{E^2}$$

$$\sigma_y^2 = \frac{R_y}{E} - \frac{Y^2}{E^2}$$

In the case of using a monolithic crystal, both DOI and scatter will cause charge sharing, however with different distributions. To separate these two factors a high order summing group (3$^{rd}$ moment, skewness) can be added according to the following formula.

$$S = \Sigma(x^3 + y^3)E_{xy}$$

Figure 6B:
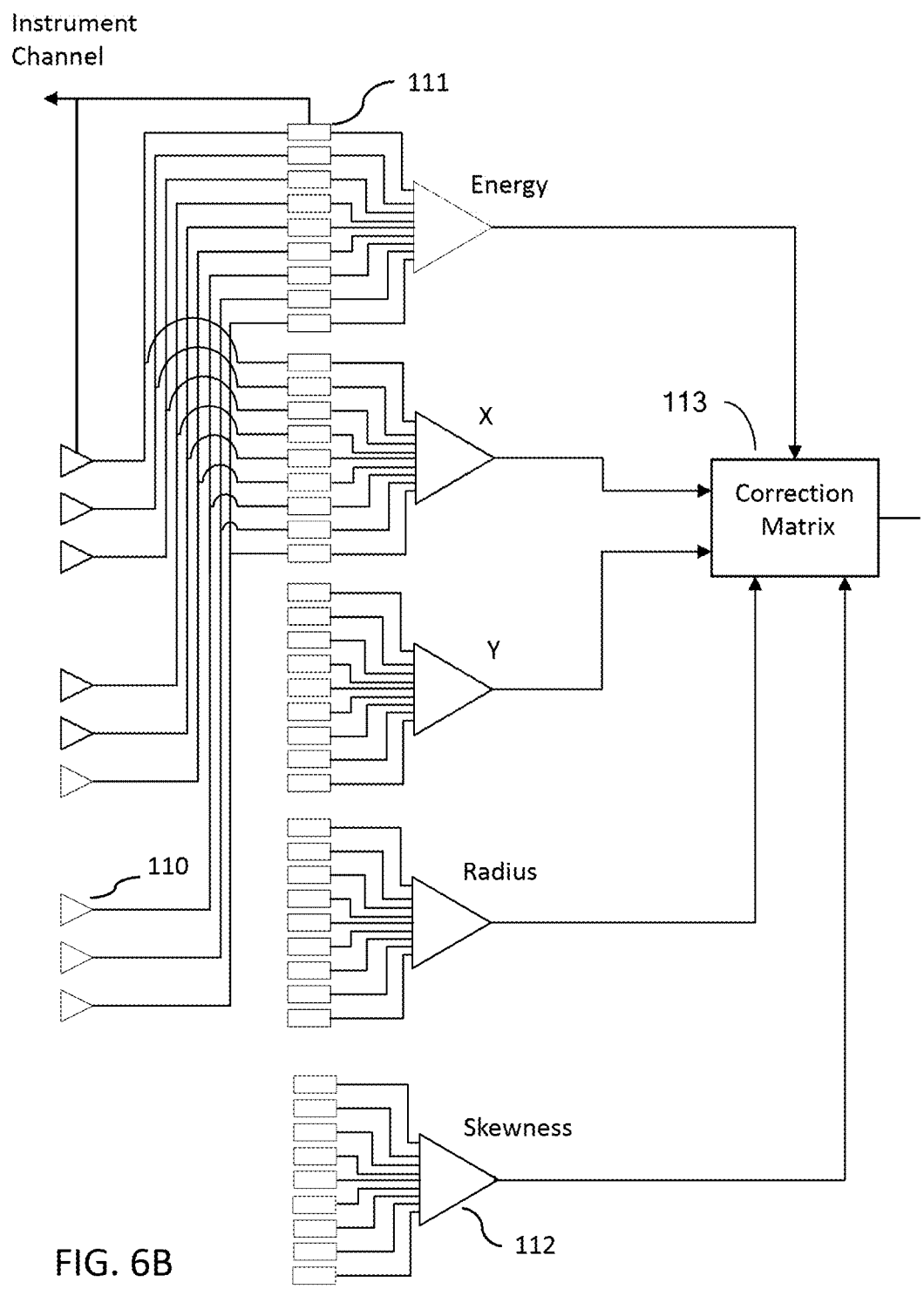
FIG. 6B is a diagram of a summing circuit according to a modification of the first embodiment according to the invention.

FIG. 6B shows an abbreviated portion of the first embodiment omitting the array and having the skewness summing circuit. Alternatively, one of the 4 groups can have the weights adjusted by processor 207 to generate the skewness signal S. Timing information can also be measured using the energy signal. The timing information can also be measured using a separate signal from the SiPM array, for example as shown in FIG. 6A where application of the bias voltage is sent to a timing channel.

Each of the outputs from the SiPMs D11-D33 is fed to the group of weighting circuits corresponding to the particular output, Energy, X, Y and Radius. A first example of the weights is shown in FIG. 9. A 4×4 SiPM array is used to illustrate the weighting. Weights are shown in the table of FIG. 9 for the X output (W_X), Y output (W_Y), Energy (W_E) and the Radius output (W_R). FIGS. 10A-10D show the weights in correspondence with the 4×4 SiPM array. As described above, the X and Y weights are proportion to the x and y positions, the Energy weights are constant, and the Radius weights vary as $(x^2+y^2)$. It is noted that the weights for the Radius are nonlinear. Such nonlinear weights could also be applied to the coordinates X and Y and energy and be tailored for better accuracy. For example, the SiPM at a certain position may have a lower gain compared to other positions, and the weights applied to the associated channel can be scaled accordingly with a factor inversely proportional to the gain of the SiPM to compensate the lower gain position of the SiPM. As a result, the weights are no longer linear to the X or Y coordinates.

Figure 11:
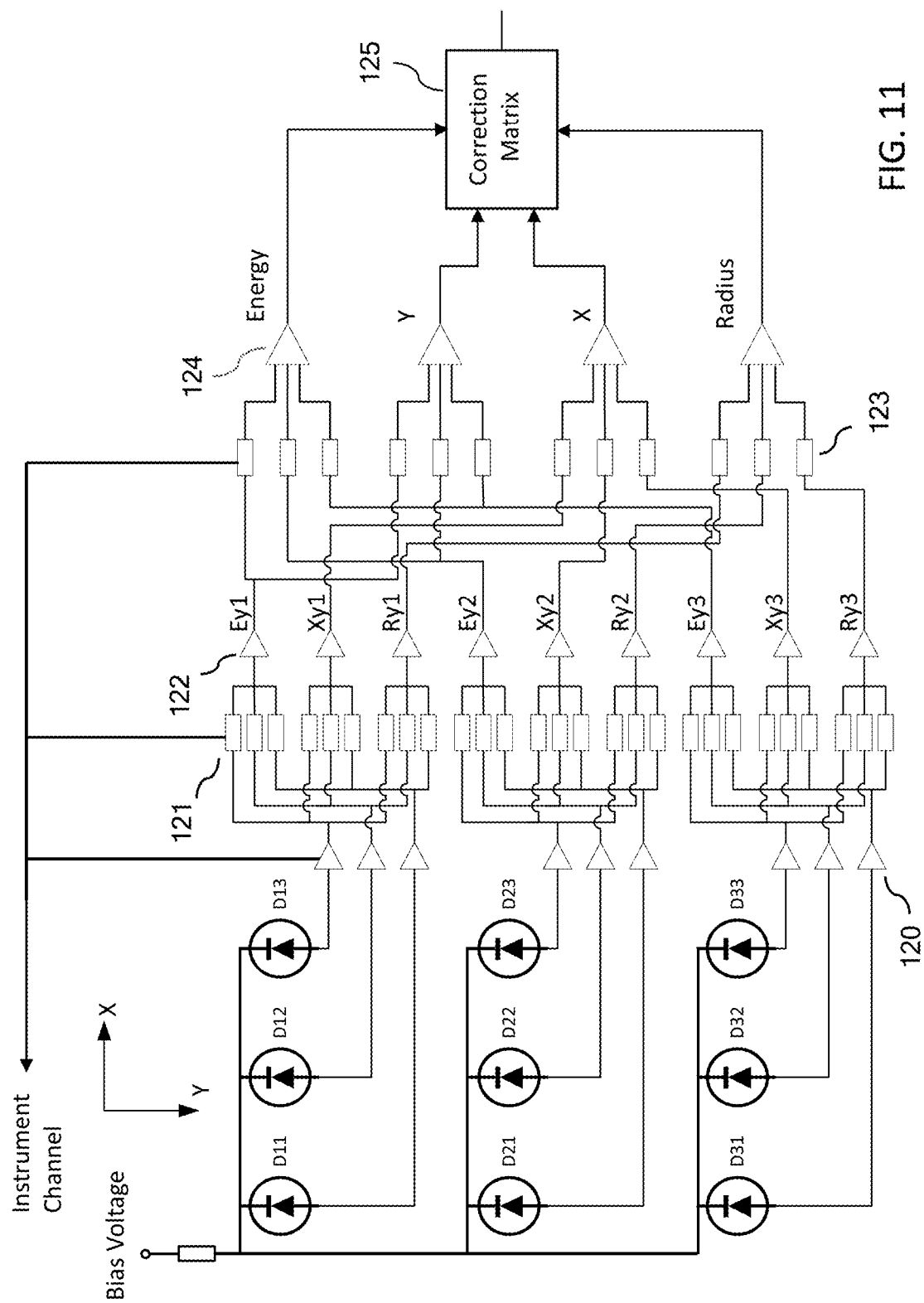
FIG. 11 is a diagram of a summing circuit according to a second embodiment of the invention.

The one-stage summing circuit of FIG. 6A requires a significant number of connections between the buffers and weight circuits. A second embodiment is shown in FIG. 11 having two-stage summing with fewer connections. A 3×3 matrix of SiPMs D11-D33 is shown for ease of illustration. Other numbers of SiPMs can be used. In this embodiment, the signals are first buffered using buffer circuits 120 and then locally weighted using weighting circuits 121. The weighted signals from weighting circuits 121 are fed to summing circuits 122 to generate a series of local energy, X, and Y signals, Ey$_n$, Xy$_n$ and Ry$_n$. In this example, the SiPMs in a row along the x direction are first summed into three signals E$_{y1}$, X$_{y1}$ and R$_{y1}$. Ey represents the total energy of the row, Xy represents the weighted x position of the row and Ry is the variance. These three signals are determined according to the following equations:

$$E_y = \Sigma_y E_{xy}$$

$$X_y = \Sigma_y x E_{xy}$$

$$R_y = \Sigma_y (x^2 + y^2) E_{xy}$$

These signals are input to weighting) circuits 123 and are then summed in summing circuits 124 to produce the Energy, X, Y and Radius signals. These signals are produced according to the flowing equations:

$$E = \Sigma E_y$$

$$X = \Sigma X_y$$

$$Y = \Sigma y E_y$$

$$R = \Sigma R_y$$

The buffer circuits 120 and weighting circuits 121 and 123 are connected to the processor 207 and DAS 208 through the instrument channel for control of the weighting values, similar to the first embodiment. Also, similar to the first embodiment a summing circuit with integrated weighting circuits, like FIG. 8, may be used.

Compared to the first embodiment, the maximum number of signals sent to the summing circuits and the number of weights needed are 3n in the 2-stage embodiment instead of $n^2$ for the 1-stage embodiment, where n is the number of SiPMs along the x direction. The number of summing amplifier is 4 for the 1-stage embodiment and 3n+4 for the 2-stage embodiment. The number of buffer amplifiers ($n^2$) is the same for the 1-stage and 2-stage embodiments. While the number of summing amplifiers is greater in the 2-stage embodiment, the number of weights needed can be significantly lower when there is a large number of SiPMs in the array. With large size arrays, the number of weights can be reduced, allowing the number of traces to be reduced in the circuit, making the design and trace routing more manageable.

FIG. 12 shows an example of position decoding. This can be applied to both of the first and second embodiments. Here, a 4×4 array is also used as an example with the weights shown in FIGS. 9 and 10A-10D. Six different cases are illustrated with a maximum of two hits per matrix for ease of explanation. FIG. 11 includes the Summed Output and the Decoded position. The Summed Output is determined from the weights:

$$X_{sum} = \Sigma x_i E_i$$

$$Y_{sum} = \Sigma y_i E_i$$

$$E_{sum} = \Sigma E_i$$

$$R_{sum} = \Sigma(x_i^2 + y_i^2) E_i$$

The Decoded Position is determined as follows:

$$PX = X_{sum}/E_{sum}$$

$$PY = Y_{sum}/E_{sum}$$

$$PE = E_{sum}$$

$$PR = \frac{R_{sum}}{E_{sum}} - \frac{X_{sum}^2 + Y_{sum}^2}{E_{sum}^2}$$

In Case 1, Hit 1 occurs at (1,1) in the matrix. The weights for X, Y and E are all 1 at location (1,1). The decoded position formation (X=Y=1) indicates that the hit occurred at (1,1). The weights for Case 2 also having Hit1 and (2,2) are each 2 for x and y and the decoded position information (X=Y=2) indicates that the hit occurred at (2,2). Cases 3-6 each include 2 hits, Hit1 and Hit2. Each of the hit positions results in a unique set of values for X, Y and R allowing the positions for each of Hit1 and Hit2 to be determined. Processor 207 can compare the calculated X, Y and R values obtained during a sampling period to stored values in memory 205 determined beforehand empirically, for example, to determine the position(s) of the hit(s). The above analysis can be carried out for other numbers of hits greater than 2 within the sampling matrix and the calculated values can be compared by processor 207 to stored values to determine the positions of the hits.

The decoding information can also be used to determine the distance between hits by understanding the positions of the detected hits by the unique combinations of the X, Y and R values. The distance information can be used to choose appropriate Time-of-Flight (TOF) and Point-Spread Function (PSF) kernels in subsequent image reconstruction to improve image quality. The timing resolution and the spatial resolution are both affected by the charge distribution. Traditionally, the image reconstruction uses average TOF and PSF kernels for all events. The present invention can supply the charge distribution information to choose appropriate TOF (for timing) and PSF (for spatial resolution) kernels for a given event.

In the first and second embodiments, the summing groups can be expressed as moments, based upon moment mathematics (Moment (mathematics)—Wikipedia). The Energy channel is the $0^{th}$ moment, or the integral. The X and Y channels are $1^{st}$ moments, or the mean. The Radius channel is the $2^{nd}$ moment, or the variance of the charge distribution across the array, which corresponds to the level of spreading of the charge.

The above formulas for the first and second embodiments to derive the moment of the charge distribution and the position of the charge deposition in crystal are in their simplest form, considering no non-uniformity in the crystals and SiPMs. In reality, variation in detector response, non-uniformity in the crystals and crystal boundaries require further correction to translate raw summed values to physical measurements. The general form to translate raw X, Y, Radius and Energy sums to physical (X,Y,Z, and Energy) values includes but not limited to a linear matrix, a product of multiple matrices, a multi-order translation table, look-up table, or a neural network. Here, Z represents either the depth of interaction, or the spatial separation of Compton hits, depending on the application.

The weights for the signals from the SiPMs can be further optimized to extract the relevant information in the most efficient and accurate manner. For example, simulated results or calibration measurements may be used to calibrate the weights. In the case of the crystal arrays (individual or slatted) the relevant information is energy, x and y position, and distance between hits from the same gamma ray. For the monolithic crystal, the relevant information may include energy, x, y, DOI and the distance between hits from the same gamma ray. The weights can also be compensated for manufacturing variance. The calibration measurements may be used for this compensation.

Figure 13:
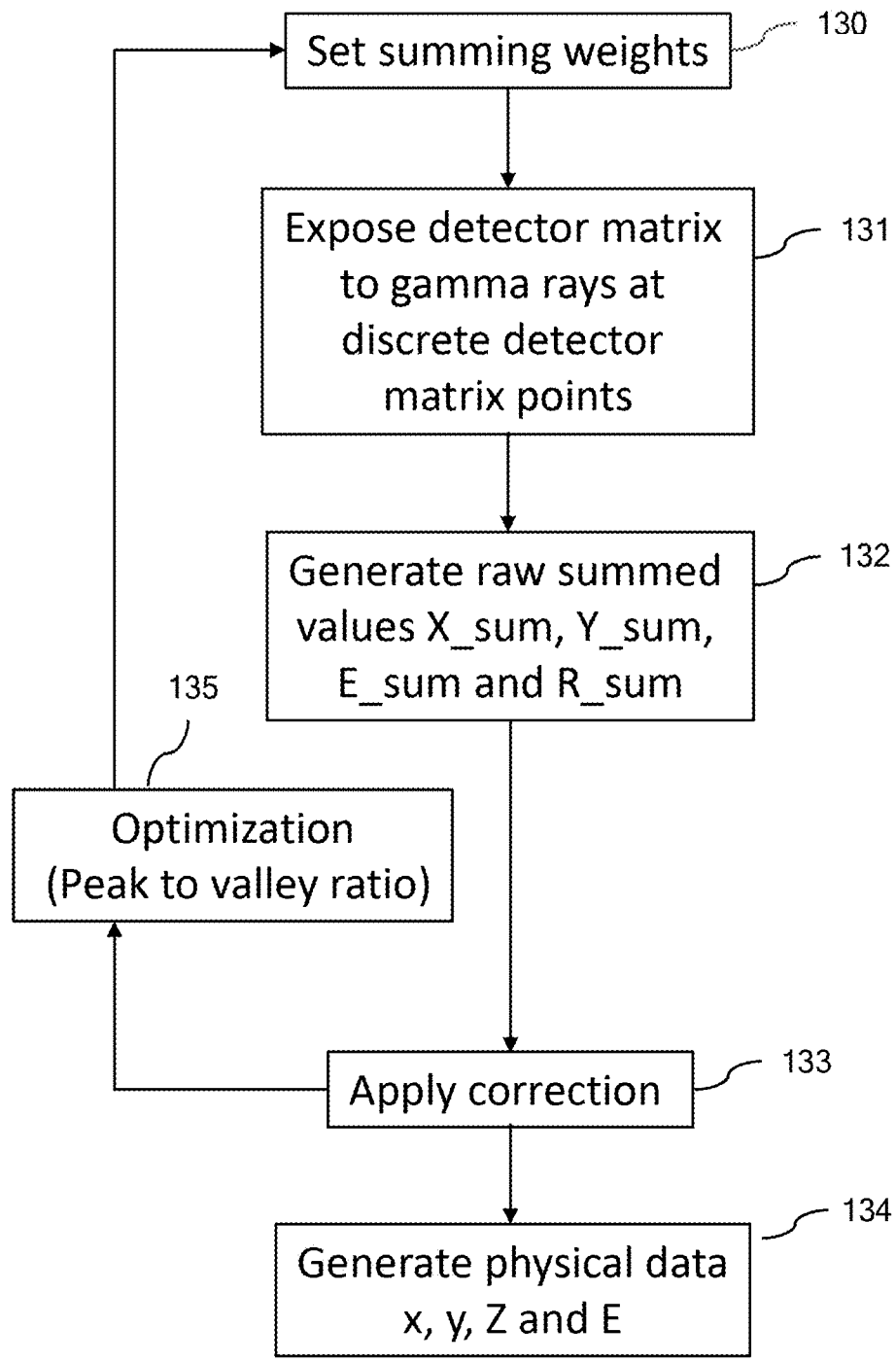
FIG. 13 is a flow chart of a method of weight adjustment and signal correction according to the invention.

FIG. 13 is a diagram illustrating a process for data processing and calibration for spatial information. In a first example, the process is applied to monolithic crystal for extracting spatial information. For the monolithic crystal, spatial information is extracted corresponding to the three-dimensional position of the gamma interaction point (x, y and z). Also, the DOI is typically extracted using the R channel along with x and y positions.

Figure 1:
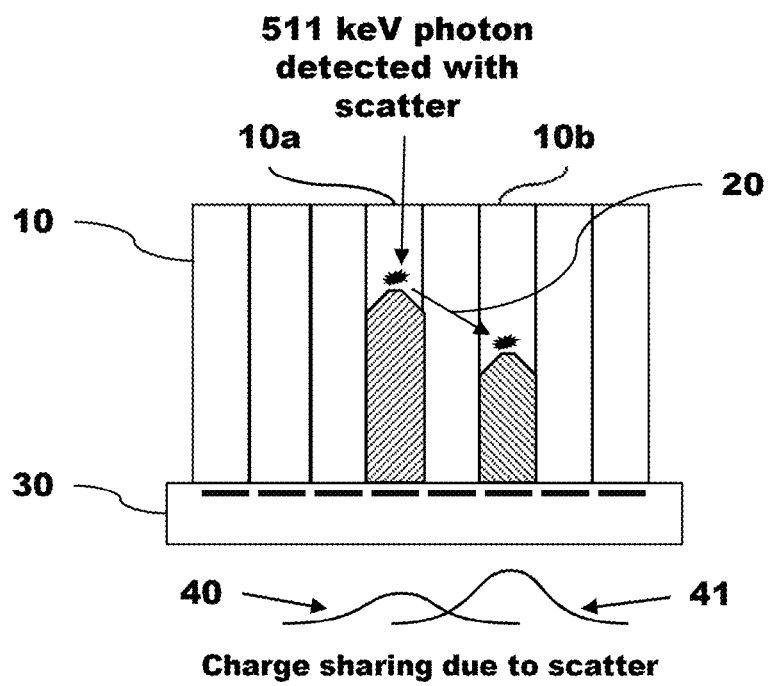
FIG. 1 is a diagram of light scattering in a crystal array.
Figure 2:
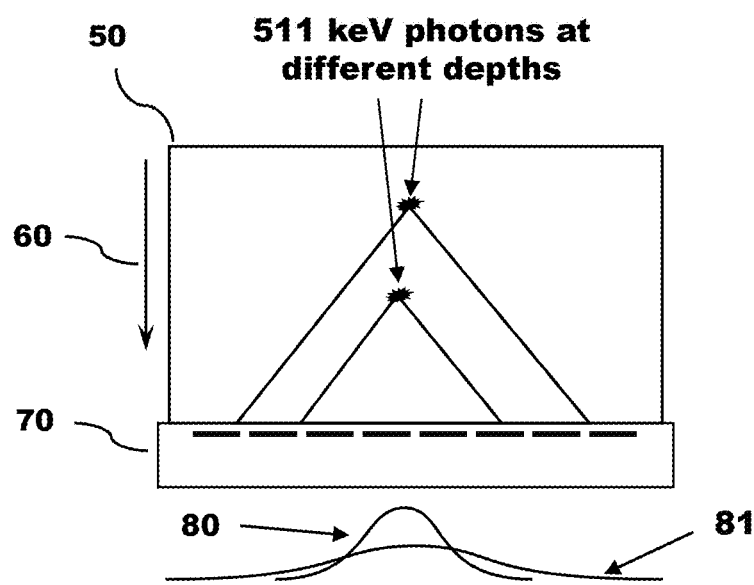
FIG. 2 is a diagram of light scattering in a monolithic crystal.

The summing weights are set in the photodetector in step 130. In step 131, the detector matrix is exposed to gamma rays by exposing a collimated gamma source, for example pinhole collimation, at discrete positions. In the system shown in FIG. 1, the collimated gamma source can be placed in bore 102 and exposed selected GRDs 101. The raw summed outputs (X_sum, Y_sum, E_sum and R_sum) are generated in step 132. The summed outputs are corrected in step 133 by processing the summed outputs with correction matrix 113/125 to generate physical variables x, y, Z and E at step 134.

Figure 14:
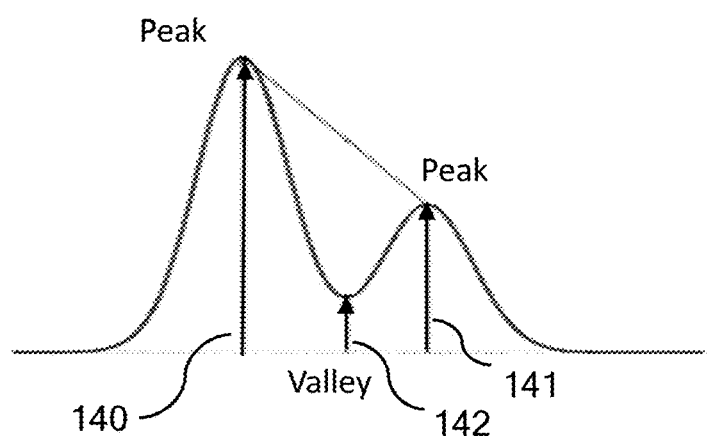
FIG. 14 is a graph illustrating signal correction according to the invention.

The weights are typically optimized to maximize the resolving power of the detector of the information desired to be extracted. In FIG. 13, an optimization process using, preferably, a performance matrix in step 135 is used which is carried out in processor 207. For the monolithic crystal where DOI or Z information is desired, one manner of optimizing the weights is to evaluate the peak-to-valley ratio of the corrected physical Z value. For example, a data set is acquired by placing collimated gamma source at two discreet depths. Referring to FIG. 14, the distribution of corrected physical Z values based on given weights is plotted. The heights 140/141 of the peaks, which represent the two calibration depths, and heights 142 valleys, which represent the ambiguousness between the two depths, are compared and the weights are optimized to maximize the peak-to-valley ratio.

The optimization can either take a trial and error method, by varying the weights and compare the outcome, and find the optimal settings through iterations. Another approach is to use modeling of the expected detector response with different weights, whereby the optimization can be achieved with fewer iterations. A similar procedure may be used for the X and Y channels.

Figure 15:
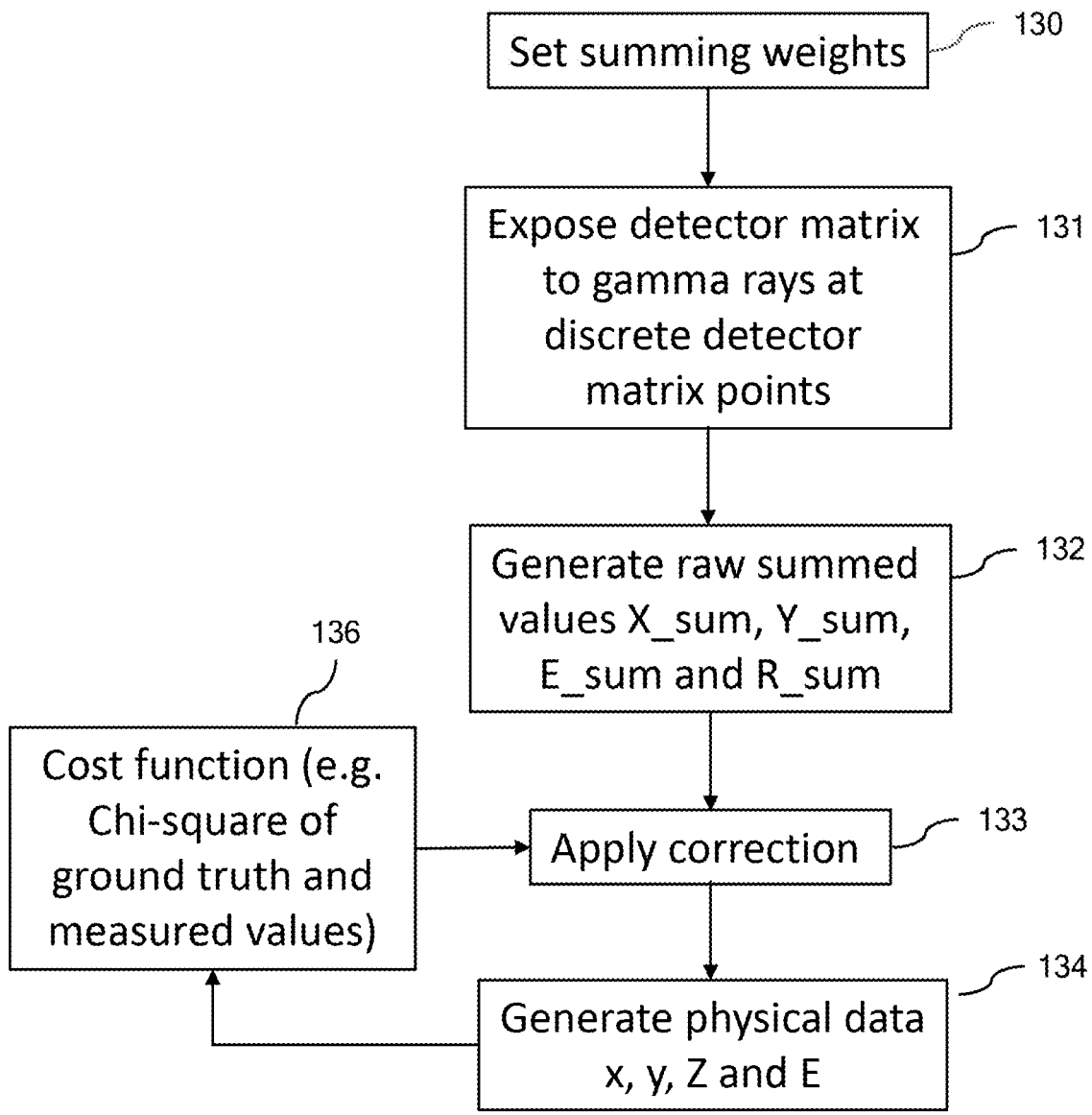
FIG. 15 is a flow chart of a method of calibrating the correction matrix.

The correction matrix is used to reconstruct the physical values close to their ground truth. Using data collected with gamma source placed at known discrete positions, one can calibrate the correction matrix by minimizing a cost function, e.g. a chi-square function between ground truth and measured values. FIG. 15 illustrates the process of calibrating the correction matrix. Steps 130-134 described above in connection with FIG. 13 are performed to produce the physical variables x, y, Z and E at step 134. At step 136, the physical values are subject to the correction by minimization of the cost function. The correction in step 136 is used to calibrate the correction performed in step 133.

With the detector response with different weights modeled, the optimization of weights and calibration of correction matrix can be performed jointly to improve overall performance and reduce steps. Future, mathematical optimization/minimization/maximization methods can be used are, but not limited to, least squire, maximum likelihood and machine learning.

The above discussion of the first and second embodiments is based upon square (n×n) arrays. The invention can also be applied to n×m arrays with an unequal number of rows and columns. It is also possible to set a weight to zero, effectively disabling part of the matrix or a channel, as desired.

While the above embodiments are directed to a PET apparatus, the embodiments are also applicable with other position sensitive gamma detectors such as single-photon emission computerized tomography (SPECT).

The present invention is able to greatly reduce the number of signals to be digitized from a photodetector array. The present invention is also able to measure the charge distribution across a detector array and provide information on the distance between scattered hits. For monolithic crystals, the present invention can also provide DOI information.

The present invention also simplifies readout design to reduce the number of digitized channels for a monolithic crystal, which typically requires readout of individual SiPMs, and can still supply the DOI information.

The present invention further allows evaluation of the DOI in crystal arrays having light sharing designs.

Obviously, numerous modifications and variations of the present invention are possible in light of the above teachings. It is therefore to be understood that within the scope of the appended claims, the invention may be practiced otherwise than as specifically described herein.

The invention claimed is:

1. A positron emission apparatus, comprising:
    a crystal configured to convert gamma rays into photons;
    a photodetector array arranged to detect the photons and to output signals based on the detected photons; and
    a circuit connected to the photodetector array comprising a plurality of summing circuits having weighting circuits, each of the summing circuits being configured to weight and sum the signals output by the array with weights determined individually for each position in a first dimension and a second dimension of the photodetector array, and the summing circuits thereby producing a first signal weighted with a constant weight as an output corresponding to a total energy of the signals, producing a second signal weighted with a weight proportion to the position in the first dimension as an output corresponding to a position of the signals in the first dimension of the photodetector array, producing a third signal weighted with a weight proportion to the position in the second dimension as an output corresponding to a position of the signals in the second dimension of the photodetector array, and producing a fourth signal weighted with a weight varying nonlinearly to the position in the first or second dimension as an output corresponding to a radius of a charge distribution of the signals, wherein:
    a first one of the summing circuits includes weighting circuits each having the same weight to produce the output corresponding to the total energy of the signals;
    a second one of the summing circuits includes weighting circuits having weights corresponding to positions in the first dimension in the photodetector array;
    a third one of the summing circuits includes weighting circuits having weights corresponding to positions in the second dimension in the photodetector array;
    a fourth one of the summing circuits includes weighting circuits having weights corresponding to a variance of the positions in the first and second dimensions of the photodetector array,
    the photodetector array comprises a matrix of photodetector elements in two dimensions, x and y, corresponding to the first and second dimensions, respectively;
    the weighting circuits in the first one of the summing circuits produces a signal E as the output corresponding to the total energy of the signals, using $E=\Sigma E_{xy}$;

the weighting circuits in the second one of the summing circuits produces a signal X corresponding to the x dimension using $X=\Sigma x E_{xy}$;

the weighting circuits in the third one of the summing circuits produces a signal Y corresponding to the y dimension using $Y=\Sigma y E_{xy}$; and the weighting circuits in the fourth one of the summing circuits produces a signal R corresponding to the charge distribution using $R=\Sigma(x^2+y^2)E_{xy}$, where $E_{xy}$ is a value of a signal from a buffer corresponding to a photodetector element at position (x,y).

2. The positron emission apparatus as recited in claim 1, comprising a processor configured to determine a summed variance of the charge distribution using $$\sigma^2 = \frac{R}{E} - \frac{X^2+Y^2}{E^2}.$$

3. The positron emission apparatus as recited in claim 1, comprising a fifth summing circuit configured to produce a signal S using $S=\Sigma(x^3+y^3)E_{xy}$.

4. The positron emission apparatus as recited in claim 1, wherein at least the weights of the weighting circuits in the fourth one of the summing circuits are non-linear with respect to a dimension of the photodetector array.

5. The positron emission apparatus as recited in claim 1, wherein the summing circuit comprises:
    a plurality of buffer circuits each configured to receive an output of one element of the photodetector array;
    a plurality of sets of weighting circuits, each weighting circuit being connected to respectively receive an output of one of the buffer circuits; and
    a plurality of summing amplifiers each of which are connected to receive an output from one set of the weighting circuits.

6. The positron emission apparatus as recited in claim 5, wherein each one of the summing amplifiers is configured to be integral with the corresponding set of weighting circuits.

7. The positron emission apparatus as recited in claim 1, wherein the summing circuit comprises:
    a plurality of buffer circuits each configured to receive an output of one element of the photodetector array;
    a plurality of sets of first weighting circuits, each set of first weighting circuits being connected to respectively receive outputs from respective groups of the buffer circuits;
    a plurality of sets of first summing amplifiers, each set of first summing amplifiers being connected to outputs from one set of the plurality of sets of first weighting circuits;
    a plurality of sets of second weighting circuits each connected to receive selected ones of outputs of the sets of first summing amplifiers; and
    a plurality of second summing amplifiers each connected to receive outputs from one set of the second weighting circuits.

8. A circuit for receiving signals from a photodetector array arranged to detect photons converted from gamma rays by a crystal and to output signals based on the detected photons, the photodetector array comprising a matrix of photodetector elements in two dimensions, x and y, corresponding to first and second dimensions, respectively, comprising:
    a plurality of summing circuits having weighting circuits, the summing circuits each being configured to weight and sum the signals from the array with weights determined individually for each position in the first dimension and the second dimension of the photodetector array, the summing circuits thereby producing a first signal weighted with a constant weight as an output corresponding to a total energy of the signals, producing a second signal weighted with a weight proportion to the position in the first dimension as an output corresponding to a position of the signals in the first dimension of the photodetector array, producing a third signal weighted with a weight proportion to the position in the second dimension as an output corresponding to a position of the signals in the second dimension of the photodetector array, and producing a fourth signal weighted with a weight varying nonlinearly to the position in the first or second dimension as an output corresponding to a radius of a charge distribution of the signals, wherein:

a first one of the summing circuits includes weighting circuits each having the same weight to produce the output corresponding to the total energy of the signals;

a second one of the summing circuits includes weighting circuits having weights corresponding to positions in a first dimension in the photodetector array;

a third one of the summing circuits includes weighting circuits having weights corresponding to positions in a second dimension in the photodetector array;

a fourth one of the summing circuits includes weighting circuits having weights corresponding to a variance of the positions in the first and second dimensions of the photodetector array;

the weighting circuits in the first one of the summing circuits produces a signal E as the output corresponding to the total energy of the signals, using $E=\Sigma E_{xy}$;

the weighting circuits in the second one of the summing circuits produces a signal X corresponding to the x dimension using $X=\Sigma x E_{xy}$;

the weighting circuits in the third one of the summing circuits produces a signal Y corresponding to the y dimension using $Y=\Sigma y E_{xy}$; and the weighting circuits in the fourth one of the summing circuits produces a signal R corresponding to the charge distribution using $R=\Sigma(x^2+y^2)E_{xy}$, where $E_{xy}$ is a value of a signal from a buffer corresponding to a photodetector element at position (x,y).

9. The circuit as recited in claim 8, comprising a fifth summing circuit configured to produce a signal S using $S=\Sigma(x^3+y^3)E_{xy}$.

10. The circuit as recited in claim 8, wherein at least the weights of the weighting circuits in the fourth one of the summing circuits are non-linear with respect to a dimension of the photodetector array.

11. The circuit as recited in claim 8, wherein the summing circuit comprises:

a plurality of buffer circuits each configured to receive an output of one element of the photodetector array;

a plurality of sets of weighting circuits, each weighting circuit being connected to respectively receive an output of one of the buffer circuits; and a plurality of summing amplifiers each of which are connected to receive an output from one set of the weighting circuits.

12. The circuit as recited in claim 11, wherein each one of the summing amplifiers is configured to be integral with the corresponding set of weighting circuits.

13. The circuit as recited in claim 8, wherein the summing circuit comprises:

a plurality of buffer circuits each configured to receive an output of one element of the photodetector array;

a plurality of sets of first weighting circuits, each set of first weighting circuits being connected to respectively receive outputs from respective groups of the buffer circuits;

a plurality of sets of first summing amplifiers, each set of first summing amplifiers being connected to outputs from one set of the plurality of sets of first weighting circuits;

a plurality of sets of second weighting circuits each connected to receive selected ones of outputs of the sets of first summing amplifiers; and a plurality of second summing amplifiers each connected to receive outputs from one set of the second weighting circuits.

14. A method of extracting information from gamma interactions within a crystal, comprising:

producing output signals from the interactions using a plurality of summing circuits each configured to receive each of the output signals;

producing a first signal weighted with a constant weight as an output corresponding to a total energy of the output signals;

producing a second signal weighted with a weight proportion to the position in a first dimension as an output corresponding to a position of the output signals in the first dimension of the crystal;

producing a third signal weighted with a weight proportion to a position in a second dimension as an output corresponding to a position of the output signals in the second dimension of the crystal;

producing a fourth signal weighted with a weight varying nonlinearly to the position in the first or second dimension as an output corresponding to a radius of a charge distribution of the output signals;

using a first summing circuit including weighting circuits each having the same weight to produce the first signal;

using a second summing circuit including weighting circuits having weights corresponding to positions in a first dimension in the crystal;

using a third summing circuit including weighting circuits having weights corresponding to positions in a second dimension of the crystal; and using a fourth summing circuit including weighting circuits having weights corresponding to a variance of the positions in the first and second dimensions of the crystal; wherein:

the weighting circuits in the first summing circuit produces a signal E as the output corresponding to the total energy of the signals, using $E=\Sigma E_{xy}$;

the weighting circuits in the second summing circuit produces a signal X corresponding to the x dimension using $X=\Sigma x E_{xy}$;

the weighting circuits in the third summing circuit produces a signal Y corresponding to the y dimension using $Y=\Sigma y E_{xy}$; and the weighting circuits in the fourth summing circuit produces a signal R corresponding to the charge distribution using $$R=\Sigma(x^2+y^2)E_{xy},$$

where $E_{xy}$ is a value of a signal from a buffer corresponding to a photodetector element at position (x,y).

15. The method as recited in claim 14, comprising:
using a plurality of buffer circuits connected to receive respective signals from the crystal;
using a plurality of sets of weighting circuits each set connected to receive each of the outputs of the plurality of buffer circuits; and
using a plurality of summing amplifiers each connected to receive outputs of one set of the weighting circuits.

16. A method of determining positions of gamma ray interactions in a crystal, comprising:
producing output signals from the interactions using a plurality of summing circuits each configured to receive each of the output signals;
producing a first signal weighted with a constant weight as an output corresponding to a total energy of the output signals;
producing a second signal weighted with a weight proportion to a position in a first dimension as an output corresponding to a position of the output signals in the first dimension of the crystal;
producing a third signal weighted with a weight proportion to a position in a second dimension as an output corresponding to a position of the output signals in the second dimension of the crystal;
producing a fourth signal weighted with a weight varying nonlinearly to the position in the first or second dimension as an output corresponding to a radius of a charge distribution of the output signal;
determining a position of an interaction using at least one of:
a ratio of the second signal to the first signal,
a ratio of the third signal to the first signal, and
a ratio of a sum of a square of the first signal and a square of the second signal to the square of the first signal subtracted from a ratio of the fourth signal to the first signal;
using a first summing circuit including weighting circuits each having the same weight to produce the first signal;
using a second summing circuit including weighting circuits having weights corresponding to positions in a first dimension in the crystal;
using a third summing circuit including weighting circuits having weights corresponding to positions in a second dimension of the crystal; and
using a fourth summing circuit including weighting circuits having weights corresponding to a variance of the positions in the first and second dimensions of the crystal; wherein:
the weighting circuits in the first summing circuit produces a signal E as the output corresponding to the total energy of the signals, using $$E=\Sigma E_{xy};$$

the weighting circuits in the second summing circuit produces a signal X corresponding to the x dimension using $$X=\Sigma x E_{xy};$$

the weighting circuits in the third summing circuit produces a signal Y corresponding to the y dimension using $$Y=\Sigma y E_{xy};\text{ and}$$

the weighting circuits in the fourth summing circuit produces a signal R corresponding to the charge distribution using $$R=\Sigma(x^2+y^2)E_{xy},$$

where $E_{xy}$ is a value of a signal from a buffer corresponding to a photodetector element at position (x,y).

* * * * *